United States Patent [19]

García-Carreé

[11] Patent Number: 5,226,433
[45] Date of Patent: Jul. 13, 1993

[54] DEVICE FOR THE TREATMENT OF INGROWING NAILS

[76] Inventor: Juan J. García-Carreé, Pau Casals 67, 3°, 1a, 088340 Sant Boi de Llobregat Barcelona, Spain

[21] Appl. No.: 894,051

[22] Filed: Jun. 3, 1992

[30] Foreign Application Priority Data

Jun. 5, 1991 [ES] Spain .............................. 910/923

[51] Int. Cl.$^5$ ............................................. A45D 24/00
[52] U.S. Cl. ....................................... 132/200; 132/73
[58] Field of Search ...................... 132/200, 73; 623/21

[56] References Cited

U.S. PATENT DOCUMENTS

| | | | |
|---|---|---|---|
| 1,135,382 | 4/1915 | Kindred | 132/73 |
| 3,228,404 | 1/1966 | Turner | 132/73 |
| 3,487,831 | 1/1970 | Jaume et al. | 132/73 |
| 4,445,234 | 5/1984 | Ogunro | 132/73 |
| 4,559,055 | 12/1985 | Ogunro | 132/73 |
| 4,625,740 | 12/1986 | Roth | 132/73 |

FOREIGN PATENT DOCUMENTS 637050  5/1950  United Kingdom .................. 132/73

*Primary Examiner*—Gene Mancene
*Assistant Examiner*—Frank A. LaViola
*Attorney, Agent, or Firm*—Wells, St. John, Roberts, Gregory & Matkin

[57] ABSTRACT

A device and process for treatment of ingrowing nails or felons includes a thin flexible inert body of flat, substantially rectangular configuration. The body is folded at least once in a first configuration to define a dihedric angular body. In another preferred form, the device is folded twice to form a double walled construction. In the present treatment, a portion of the nail is first separated from the affected underlying epidermis area of the affected finger or toe. Next, the device is held with the fold thereof aligned with the released edge of the nail, and is inserted over the released edge of the nail. The nail is received between facing surfaces of the device, with the released nail edge extending inside the fold between the facing surfaces. The device is positioned such that the folded surfaces of the device overlap the affected area and the released nail edge is held away from the affected area. The device is allowed to remain in position on the nail until the affected area heals and then for an extended time beyond initial healing to assure rehabilitation of the adjacent tissues before the nail is allowed contact, thereby avoiding a relapse.

10 Claims, 5 Drawing Sheets

DEVICE FOR THE TREATMENT OF INGROWING NAILS

TECHNICAL FIELD

The present invention refers to a device and process for treatment of ingrowing nails or felons.

BACKGROUND OF THE INVENTION

As notoriously known, many people undergo hand or foot ailments called red nails, ingrown nails, or felons. These painful ailments consist of ulceration caused through incorrect introduction of the toe or fingernail into adjacent tissues at the side part of the nail. This action causes pain, particularly in the toes and especially while walking or using the hands, since such an incorrect introduction of the nail into the flesh encourages toe or finger nerves to be sorely excited.

Although there are surgical treatments to correct ingrowing nails or felons, it is desirable for this ailment to be duly corrected with simpler means without surgery. Even minor surgery and the associated local anesthesia used for such ailments is expensive, time consuming, and worrisome to the afflicted patient. It therefore becomes desirable for a treatment and apparatus that may be self applied. Such treatment is entirely possible by using the device and process of this invention, which allows the ingrowing nail or felon treatment to be performed even by non-qualified individuals.

The invention as further described herein includes application of a body to the affected nail, previously released at one of its sides. The applied body prevents direct contact of the nail edge with the respective inflamed finger or toe tissues normally situated below the invading nail.

In this way the ingrowing nail or felon's effect and consequences are removed and the pain, caused by this abnormal condition, disappears.

To facilitate further the disclosure, the present description is accompanied by drawings showing an illustrative and non-exhaustive examples of a device for, and the treatment of, ingrowing nails or felons.

BRIEF DESCRIPTION OF THE DRAWINGS

Preferred embodiments of the invention are described below with reference to the accompanying drawings, in which.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

The device disclosed herein includes a thin and flexible laminar body 1 made with a biologically inert, mechanically resistant material. There term "mechanically resistant" should be understood as relating to that property of the body that resists scratching and is often referred to in the engineering arts as "hardness". This property is important to the present invention, to enable the device to withstand substantially permanent contact with the nail edge, especially while walking in the case of a toe, or while working with gloves on in the case of a finger or thumb. Elasticity or resilience are least desirable properties of the material, since they tend to put the device out of place sooner or later. The material must also have plasticity while maintaining a sufficient degree of hardness. To meet the above requirements, unalloyed aluminum or polyethylene plastic have been found useful (with dimensions as identified below).

Figure 1:
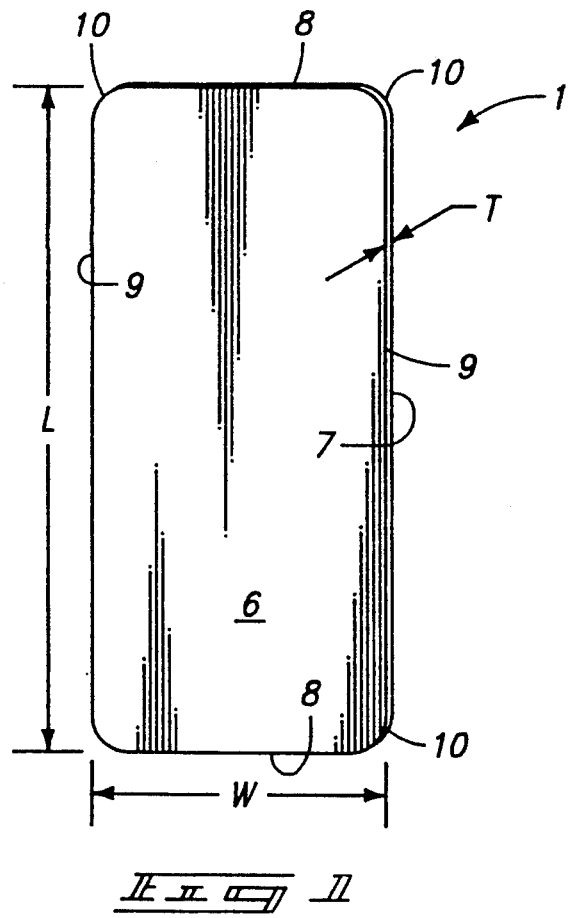
FIG. 1 is an enlarged view of a flat flexible unfolded body, prior to being selectively folded to a configuration as shown by FIGS. 2 or 3.

The body of the present invention as generally shown in FIG. 1 is specially provided to be formed into either of two preferred configurations exemplified in the drawings.

Figure 2:
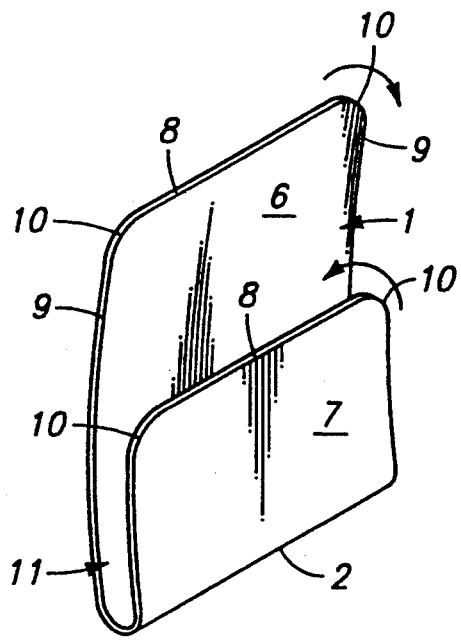
FIG. 2 shows the body in a first folded form.
Figure 5:
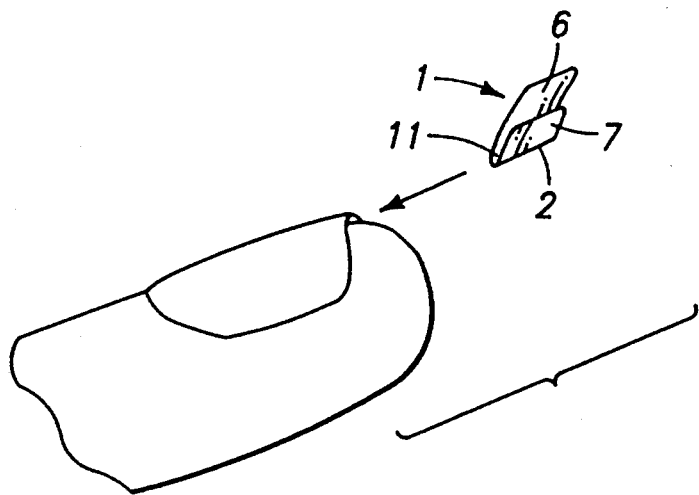
FIGS. 5 and 6 show phases of a preferred process for treatment using the present device in the first folded form.
Figure 6:
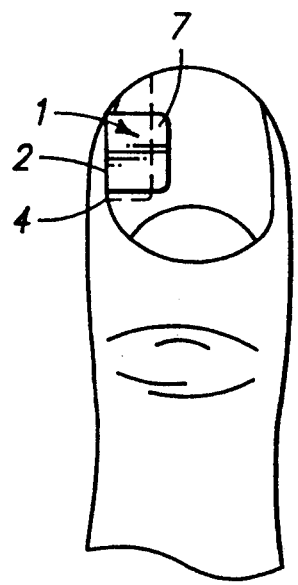

A first preferred configuration is exemplified in FIGS. 2, 5 and 6, and a second preferred configuration is shown in FIGS. 3 and 7-10.

Both folded forms are constructed from the thin, generally rectangularly shaped body 1, which includes a length dimension "L" (FIG. 1) between end edges 8 and a width dimension "W" between side edges 9. The bodies also include thickness dimensions between opposed faces 6, 7.

The sides and end edges of the body are joined by corners 10 that are rounded to avoid traumatizing tissues when the device is inserted using the process steps as shown in FIGS. 5-9. The rounded corners also avoid traumatizing tissues when the devices is removed following the treatment process.

A preferred range of width, length, and thickness dimensions of the body 1 for folding into the first or second forms are given (in millimeters) in the chart appearing below.

Figure 3:
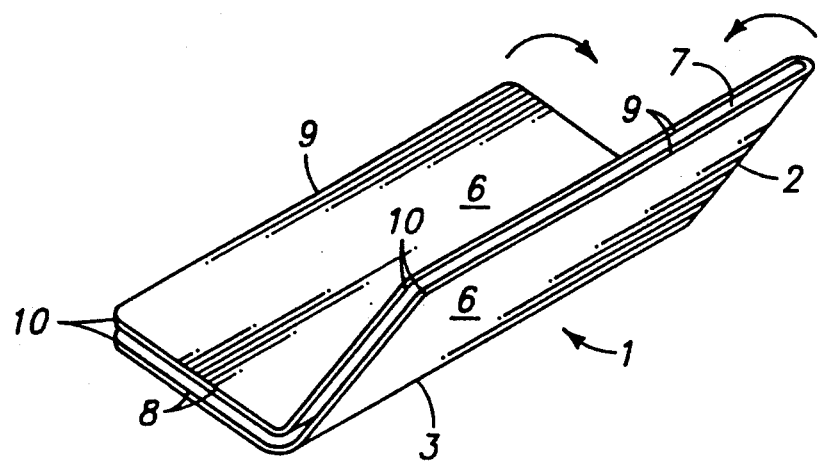
FIG. 3 shows the body in a second folded form.

| Dimension = mm | For FIG. 2 Form | For FIG. 3 Form |
| --- | --- | --- |
| Length "L" | 10 to 20 mm | 10 to 30 mm |
| Width "W" | 5 to 15 mm | 8 to 16 mm |
| Thickness "T" | 0.08 to 0.16 mm | 0.04 to 0.08 mm |

The length, width and thickness dimensions are variable with the material and the folded form to be used. For example, a device with the first folded configuration is advantageously formed of unalloyed aluminum with a thickness dimension of about 0.1 mm and length and width dimensions in the range indicated in the chart above in the "FIG. 2" column.

The FIG. 3 configuration lends itself best to plastic materials (advantageously polyethylene) of about 0.05 mm thickness, and with width and length dimensions as indicated in the chart by the "FIG. 3" column.

The various width and length dimensions indicated for the device are responsive to the need for versatility, due to variances in individuals, primarily in size of the affected areas. A child's nail, for example, is typically smaller than an adult. Further, there are physical nail size variances within individuals themselves. A thumb nail, for example, is typically larger than a 5th or "little finger" nail; toe nails may be even smaller. The size range variances shown in the chart are provided to accommodate a reasonable range of such variances.

The body, folded to the first preferred form includes a single fold 2 extending across the body 1 between longitudinal side edges 9. The fold is preferably approximately parallel to the end edges 8 of the body or transverse to the body length dimension.

It is pointed out that the fold need not be centered on the body 1, but may be asymmetric as shown in FIG. 2. The location is dependent upon the nature and depth of the affected area of the ingrowing nail or felon.

The body thus folded to the first form includes a dihedric angular shape with a nail receiving space 11 formed between facing nail receiving areal surfaces. In the example illustrated the nail receiving areal surfaces are formed by body surface 6, however the opposite surface 7 could be as easily used, depending upon the direction of the fold.

The distance between the facing nail receiving surfaces is to be approximately equal to the thickness of the affected nail. Further, the curvature of the fold 2 is advantageously made similar to the curvature of the affected nail edge 4. Also, the body itself may be selectively formed (FIG. 2) to closely conform to the curvature of the affected nail.

FIG. 2 indicates a preliminary first fold 2 that, when complete, may result in the first preferred folded configuration. An additional fold leads to the second preferred folded configuration (FIG. 3).

FIG. 3 shows the second preferred configuration partially folded, with arrows indicating the direction of folding about the second fold 3 toward a completed fold which is shown diagrammatically in FIGS. 7-10.

The second folded form includes the original first fold 2 but also includes a longitudinal second fold 3. The second fold 3, as shown, extends longitudinally between the end edges 8 of the body.

Figure 7:
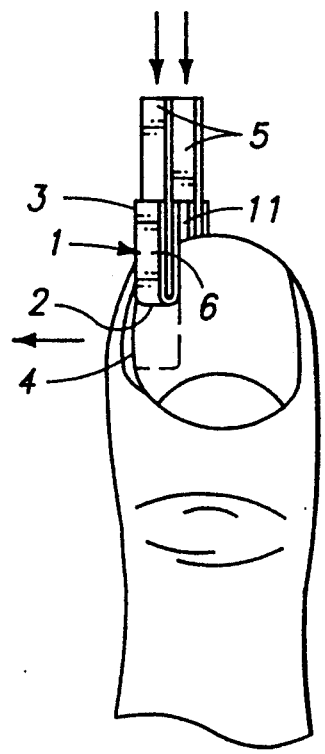
FIGS. 7-10 show phases of a preferred process for treatment using the present device in the second folded form, the thickness dimension being exaggerated for visual clarity.

The body is thus folded twice as shown to form the nail receiving space 11 between facing surfaces as shown in FIG. 7. This double fold configuration also provides for tool receiving pockets on opposite sides of the nail receiving space 11. The double wall construction is especially advantageous in application and to better space the nail from the affected tissue.

The double walls form tool receiving pockets to receive the ends of application tools 5, which may simply be small flat ended bars. The bars are used to push the device longitudinally onto the nail as shown in FIG. 7.

Figure 4:
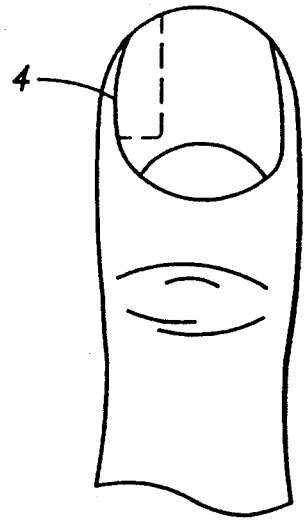
FIG. 4 shows a side area of a finger or toe affected by an ingrowing nail or felon with an area shown by dashed lines where the present device is to be applied.

Prior to application of the device, a portion of the nail shall be stripped off from the underlying epidermis at an area of the affected side as shown in FIG. 4 (dashed line). If appropriate care is taken, pain is minimized and the application can be carried out with a suitable surgical tool or even a simple manicurist's tool.

In the first preferred form of the present device, the treatment process includes bending the body 1 at a single bend line 2 that is approximately parallel to the body ends. A dihedric angular body is thereby obtained, with a formed nail receiving space between facing surfaces of the device that is capable of receiving the nail side edge 4 that has been previously released from the underlying tissues of the affected finger or toe as shown in FIG. 4.

The body 1 is selectively bent and formed to assume the shape of the affected portion of the nail. The bend line 2 may be selectively located along the length of the body, 1, depending upon the depth of the released nail area (FIG. 4). As shown in FIG. 2, the entire body may be bent or formed to accommodate the characteristics of the affected nail, such as thickness and curvature.

The properly folded device is next placed around the released edge of the nail. It may be desirable, before attaching the device, to apply an appropriate lubricant or antibiotic cream on the device to aid insertion. "Vaseline" has been found acceptable for this purpose. The insertion process involved then includes the steps of: (1) holding the device with the fold substantially aligned with the released edge of the nail (FIG. 5); (2) inserting the device in the direction shown in FIG. 5 over the nail with the nail being received with the nail receiving space 11, and with the nail edge 4 extending along the inside radius of the previously formed fold 2; (3) positioning the device on the nail such that the released nail edge 4 is held within the device and the outwardly folded areal surfaces of the device overlap the nail area previously stripped of the underlying epidermis, and with the nail edge held away from the affected are; and (4) leaving the device in position until the affected area heals. In addition to step (4), a further step is to leave the device in place for an extended period of time on the affected nail, even after healing takes place. This step is important since the newly formed tissues which appear after cicatrizing are initially weak and cannot withstand contact with the nail's edge until they mature. This is indeed a reason why felons do not usually heal on their own without some form of medical intervention.

Preferably the inserting step is accomplished in the direction indicated in FIG. 4, with the device being applied from the anterior extremity of the nail, from the distal end of the finger or toe toward the cuticle. This is accomplished in a way such that one of folded "wings" remains along the outside surface of the nail, and the other face 7 is located inside, between the nail and the affected tissues.

The device thus applied and positioned prevents the nail edge from contacting and growing into the adjacent flesh. Further, the bent or folded portion of the device is now positioned adjacent the affected tissues, presenting a much larger and smooth surface area of contact for relief from the irritation and pressure caused by the narrower invading nail edge.

Application on the nail affected side part 4, according to the device folded into the second form shown in FIG. 3 may best be accomplished using clamps or equivalent tools 5. Applying the device in the configuration shown in FIG. 3 is accomplished after the initial steps of folding the body onto itself twice; first substantially along the first fold 2, then along the selected second longitudinal fold 3 to arrive at the desired shape. Again, the locations of the folds are selected according to the nail and the excavated area under the nail. This form may also be shaped to conform to the nail configuration and the size to the affected area.

It should be noted at this point that the device is shown diagrammatically in FIGS. 7-10 with an exaggerated wall thickness dimension for clarity of illustration. Actually, the body 1 would be much thinner, as indicated by the chart above.

The application steps involved are shown in FIGS. 7-10, following the step of separating the nail edge from the affected area of the finger or toe. The tools 5 are first positioned to hold the device 1 as shown in FIG. 7 to facilitate application in the preferred direction. A lubricant may be applied to the body to facilitate the insertion step, as described above. Insertion takes place by aligning the nail receiving space 11 and by sliding the device onto the nail so the nail is received in the space 11 between the folded sections (FIG. 7). The rounded fold 2 eases the application.

Figure 8:
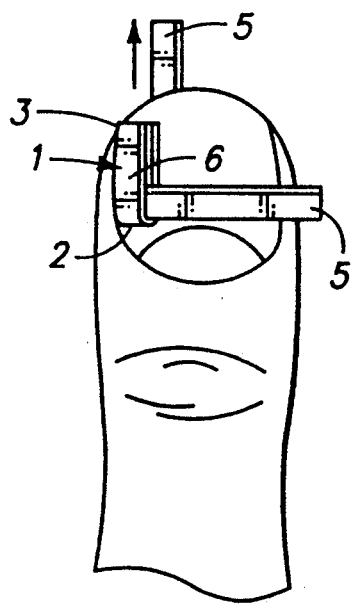
Figure 9:
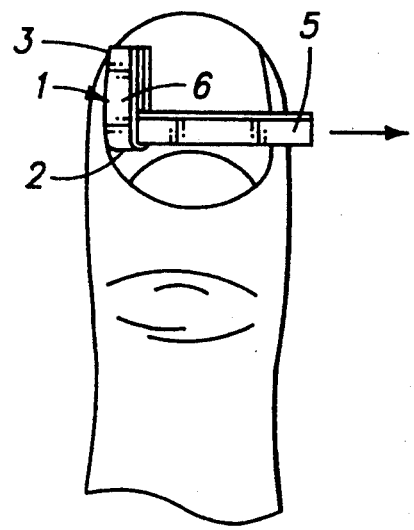
Figure 10:
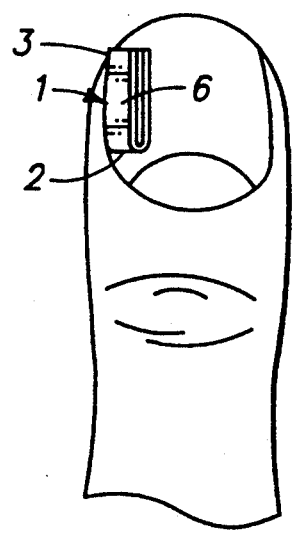

FIGS. 8 and 9 show the steps that may be utilized to best separate the device from the tools 5 following desired placement of the device. FIG. 8 shows one of the tools rotated to an orientation transverse to the finger or toe. The rotated transverse tool 5 is there used to hold the device stationary while the other tool 5 is removed as indicated by the arrow in FIG. 5. Next, the transverse tool 5 is pulled clear of the device in the direction of the arrow shown in FIG. 6, thereby leaving the device in the desired position on the finger or toe nail.

Alternatively, the device in the second folded form may be applied using another device folded substantially as shown in FIG. 2 and used as the application tool. It is also possible to simply apply the device without the aid of tools 5 or another folded device.

Once applied, the device 1 can remain positioned for a considerable length of time without adversely affecting the finger or toe tissues where it is applied. To the contrary, the device assists the healing process by holding the offending nail apart from the affected tissue. The device should remain in place until infection and inflammation completely disappear, with an additional period standing to avoid any chance of relapse.

When the inflammation disappears and the tissues have regained normal health and strength, the device may be drawn out, with the inert character and smooth wall surfaces thereof assuring that adjacent tissues will not be irritated or traumatized by the withdrawal. This is a very simply process that the patient may easily perform alone.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted in accordance with the doctrine of equivalents.

I claim:

1. A device for treatment of an affected area of an ingrowing nail or felon, comprising:
   a thin flexible inert body including longitudinal side edges and transverse end edges joining the longitudinal side edges;
   opposed areal surfaces bounded by the side and end edges;
   wherein the body includes a first fold formed transversely across the body between the longitudinal side edges; and
   a second fold formed longitudinally along the body between the transverse end edges, thereby forming an angular body with insertion tool receiving pockets formed therein and defining a nail receiving space between the pockets for slidably receiving a nail side edge and for spacing the nail side edge from the affected area;
   whereby the nail is separated from the affected area.

2. The device for treatment of ingrowing nails or felons, as claimed by claim 1 wherein the body includes a length dimension along the side edges of between approximately 10 and 30 millimeters, a width dimension along the end edges of between approximately 8 and 16 millimeters, and a thickness dimension between the opposed area surfaces between approximately 0.04 and 0.08 millimeters.

3. The device for treatment of ingrowing nails or felons, as claimed by claim 1 wherein the body includes a length dimension along the side edges of between approximately 10 and 30 millimeters.

4. The device for treatment of ingrowing nails or felons, as claimed by claim 1 wherein the body includes a length dimension along the side edges of between approximately 10 and 30 millimeters, a width dimension along the end edges of between approximately 8 an d16 millimeters.

5. The device for treatment of ingrowing nails or felons, as claimed by claim 1 wherein the body includes a thickness dimension between the opposed areal surfaces between approximately 0.04 and 0.08 millimeters.

6. The device for treatment of ingrowing nails or felons, as claimed by claim 1 wherein the body is formed of aluminum.

7. The device for treatment of ingrowing nails or felons, as claimed by claim 1 wherein the body is formed of aluminum; and includes opposed areal surfaces spaced apart by a thickness dimension of approximately 0.05 millimeters.

8. The device for treatment of ingrowing nails or felons, as claimed by claim 1 wherein the body is formed of polyethylene.

9. The device for treatment of ingrowing nails or felons, as claimed by claim 1 wherein the body is formed of polyethylene and includes opposed areal surfaces with a thickness dimension between the areal surfaces of approximately 0.05 millimeters.

10. A process for treatment of ingrowing nails or felons using a device including a thin flexible inert body of flat, substantially rectangular configuration, bent at least once to form a fold at its approximate center to define a dihedric angular body, comprising the steps of:
   releasing an edge of the affected nail;
   holding the device with the fold thereof substantially aligned with the released edge of the nail;
   inserting the device over the nail with the nail being received within a nail receiving space between facing surfaces of the device and with the released nail edge extending along inside the fold;
   positioning the device on the nail such that the released nail edge is held within the device and with outwardly facing surfaces of the device overlapping the affected area and with the nail edge held away from the affected area; and
   leaving the device in position on the nail until the affected area heals.

* * * * *

UNITED STATES PATENT AND TRADEMARK OFFICE
CERTIFICATE OF CORRECTION

PATENT NO. : 5,226,433
DATED : July 13, 1993
INVENTOR(S) : Juan Jose Garcia-Carre It is certified that error appears in the above-indentified patent and that said Letters Patent is hereby corrected as shown below:

On the title page, Item [19] "Garcia-Carree" should read --Garcia-Carre--.

Item [76] Inventor's name should read --Juan J. Garcia-Carre--

Item [30] Foreign Priority Data should read --9101923--.

Signed and Sealed this

Twelfth Day of April, 1994

BRUCE LEHMAN

*Commissioner of Patents and Trademarks*

*Attest:*

*Attesting Officer*